US008614255B2

(12) United States Patent
Blizzard et al.

(10) Patent No.: US 8,614,255 B2
(45) Date of Patent: Dec. 24, 2013

(54) PULMONARY PHARMACEUTICAL FORMULATIONS

(75) Inventors: Charles D. Blizzard, Westwood, MA (US); Michael M. Lipp, Framingham, MA (US); Kevin L. Ward, Arlington, MA (US); Rachel Ryznal, North Oxford, MA (US); Daniel Leblanc, Wellesley, MA (US); Mark Tracy, Arlington, MA (US); Rebecca Martin, Blacksburg, VA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 541 days.

(21) Appl. No.: 12/195,878

(22) Filed: Aug. 21, 2008

(65) Prior Publication Data

US 2009/0105201 A1    Apr. 23, 2009

Related U.S. Application Data

(60) Provisional application No. 60/957,108, filed on Aug. 21, 2007.

(51) Int. Cl.
*A01N 25/00* (2006.01)
*A61K 47/00* (2006.01)
*A61K 9/50* (2006.01)

(52) U.S. Cl.
USPC ........... 514/778; 514/781; 514/958; 514/970; 424/499

(58) Field of Classification Search
None
See application file for complete search history.

(56) References Cited

U.S. PATENT DOCUMENTS

| 5,674,860 | A | 10/1997 | Carling et al. |
| 2004/0067920 | A1 | 4/2004 | Leonard et al. |
| 2004/0253307 | A1 | 12/2004 | Hague et al. |
| 2005/0152847 | A1* | 7/2005 | Trofast et al. ................... 424/46 |
| 2007/0105872 | A1 | 5/2007 | Denton et al. |

OTHER PUBLICATIONS

The Calorie Control Council, "Hydrogenated Starch Hydrolysate", http://www.caloriecontrol.org/sweeteners-and-lite/polyols/hsh, accessed Jul. 26, 2012.*
Sweet Poison, "Hydrogenated Starch Hydrolysate", http://sweetpoison.wikidot.com/hydrogenated-starch-hydrolysate, accessed Jul. 26, 2012.*

* cited by examiner

*Primary Examiner* — James D Anderson
*Assistant Examiner* — Stephanie Springer
(74) *Attorney, Agent, or Firm* — Darlene A. Vanstone, Esq.; Carolyn S. Elmore, Esq.; Elmore Patent Law Group, P.C.

(57) ABSTRACT

The present invention provides improved pharmaceutical formulations for pulmonary delivery having improved chemical and physical stability of the therapeutic, prophylactic or diagnostic agent as compared to formulations known in the art. The improved pharmaceutical formulations of the invention for administration to the respiratory system of a patient for the treatment of a variety of disease conditions comprise a mass of biocompatible particles comprising an active agent, and a hydrogenated starch hydrosylate (HSH). The improvement over the prior art comprises the presence of HSH in the pharmaceutical formulation. The invention further relates to a method of treating diseases comprising administering the pharmaceutical formulations of the present invention to the respiratory system of a patient in need of treatment.

19 Claims, No Drawings

PULMONARY PHARMACEUTICAL FORMULATIONS

TECHNICAL FIELD

The invention generally relates to pharmaceutical formulations suitable for inhalation having improved physical and chemical properties, and to methods for treating, preventing and diagnosing diseases using such formulations.

BACKGROUND OF THE INVENTION

Pulmonary delivery of therapeutic, diagnostic and prophylactic agents provides an attractive alternative to oral, transdermal and parenteral administration. Pulmonary administration can typically be completed without the need for medical intervention (self-administration), the pain often associated with injection therapy is avoided, and the amount of enzymatic and pH mediated degradation of the bioactive agent, frequently encountered with oral therapies, can be significantly reduced. In addition, the lungs provide a large mucosal surface for drug absorption and there is no first-pass liver effect of absorbed drugs. Further, it has been shown that high bioavailability of many molecules, for example, macromolecules, can be achieved via pulmonary delivery or inhalation. Typically, the deep lung, or alveoli, is the primary target of inhaled bioactive agents, particularly for agents requiring systemic delivery.

Pharmaceutical formulations for respiratory delivery are known to be particularly useful for the delivery of proteins and peptides which are difficult to administer by other routes. Proteins and peptides are known to present formulation challenges due to a variety of reasons including their susceptibility to destabilization by physical and chemical factors during the formulation process and during subsequent storage. Thus, pharmaceutical formulations suitable for delivery to the respiratory system having improved physical and chemical stability are desirable.

SUMMARY OF THE INVENTION

The present invention provides improved pharmaceutical formulations for pulmonary delivery having improved chemical and physical stability of the therapeutic, prophylactic or diagnostic agent (also referred to herein interchangeably as "bioactive agents," "medicaments" or "drugs") as compared to formulations known in the art. Such improved formulations provide numerous advantages including but not limited to, more reliable pulmonary delivery of the drug, ease of manufacturing, and improved storability even in environmental conditions that would normally destabilize the drug. The improved pharmaceutical formulations of the invention for administration to the respiratory system of a patient for the treatment, prevention and diagnosis of a variety of disease conditions comprise a mass of biocompatible particles comprising an active agent and a hydrogenated starch hydrosylate (HSH). The improvement over the prior art comprises the presence of HSH in the formulation. The invention further relates to a method of treating diseases comprising pulmonary administration to the respiratory tract e.g., deep lung, central airways and/or upper airways of a patient in need of treatment an effective amount of the pharmaceutical formulations of the present invention.

DETAILED DESCRIPTION OF THE INVENTION

The present invention is based, at least in part, on the discovery that the chemical and physical stability of pharmaceutical formulation administrable by inhalation is improved by including a hydrogenated starch hydrosylate (HSH) in the formulation. In the development of pharmaceutical formulations for delivery to the respiratory system, the physical and chemical stability of such formulations under a variety of storage conditions is essential to the ultimate performance of the drug upon administration to the respiratory system. Given that many inhalable drugs are self-administered by the patient and thus stored by the patient, such drug formulations are often exposed to environmental conditions that are not ideal for long term storage prior to self-administration by the patient. Thus it is critical that the drug maintain physical and chemical stability under a variety of less than ideal or adverse conditions such that when the patient eventually administers the formulation, the integrity and percentage of the active agent actually delivered to the patient is maintained as compared to the drug formulation that is stored under "ideal" storage conditions.

Various aspects of the invention are described in further detail in the following subsections.

Compositions and Pharmaceutical Formulations

In one embodiment of the pharmaceutical formulation of the present invention includes a therapeutic, prophylactic or diagnostic agent, preferably, parathyroid hormone or a fragment thereof and a hydrogenated starch hydrolysate (HSH), preferably polyalditol, Particularly preferred are particles that include more than about 1 weight percent (wt. %) of a therapeutic, prophylactic or diagnostic agent, for instance, at least 1-50 weight percent of parathyroid hormone or a fragment thereof. In one embodiment, the particles include at least 1, 2, 3, 4, 5, 10, 15, 20, 25, 30, 35, 40, 45, 50, 55, 60, 65, 70, 75, 80, 85, 90 or 95 wt. % of parathyroid hormone or a fragment thereof. In one preferred embodiment the particles further comprise a buffering agent, preferably a hydroxytricarboxylic acid or a salt thereof, such as citrate or sodium citrate. In another preferred embodiment, the particles comprise an amino acid, such as leucine. In other embodiments, the presence of any combination of an HSH and/or a buffering agent, such as a hydroxycarboxylic acid or a salt thereof and/or a hydrophobic amino acid, as described herein, facilitates a lower percentage of the therapeutic, prophylactic or diagnostic agent while maintaining favorable features e.g., stability of the drug formulation.

In a preferred embodiment of the invention, the pharmaceutical formulations are in the form of a dry powder suitable for inhalation. A "dry powder" or "powder" as used herein with regard to the particles and the formulations of the invention means that the moisture content of the mass of particles is generally below about 10% by weight of water, more preferably below about 5% by weight of water and preferably less that about 3% by weight of water.

The therapeutic, prophylactic or diagnostic agents when released in vivo, possesses the desired biological activity, for example, therapeutic and/or prophylactic properties in vivo. The active agents in accordance with the invention can have a variety of biological activities, such as bone resorption-stimulating activity, glucoregulatory or antidiabetic activity. Suitable biologically active agents include, but are not limited to, PTH, PTH(1-84), rhPTH-(1-84) (Allelix Biopharmaceuticals), PTH fragments including but not limited to, rhPTH (1-34), teriparitide(rDNA origin) recombinant parathyroid hormone (1-34) (FORTEO.™, Eli Lilly & Co), hPTH (1-34), hPTH(1-31) and monocyclic hPTH (1-31) (Andreassen et al), additional PTH fragments and analogs thereof, for example, Ostabolin and Ostabolin-C.™, (Zelos Therapeutics, Waltham, Mass.) as well as other C-terminal PTH fragments and N-terminal PTH fragments hereinafter collectively referred to as PTH, glucagon, Glucagon-Like Peptides such as, GLP-1, GLP-2 or other GLP analogs, derivatives or agonists of Glucagon Like Peptides, exendins such as, exendin-3 and exendin-4, derivatives, agonists and analogs thereof, vasoactive intestinal peptide (VIP), immunoglobulins, antibodies, cytokines (e.g., lymphokines, monokines, chemokines), interleukins, macrophage activating factors, interferons, erythropoietin, nucleases, tumor necrosis factor, colony stimulating factors (e.g., G-CSF), insulin, enzymes (e.g., superoxide dismutase, plasminogen activator, etc.), tumor suppressors, blood proteins, hormones and hormone analogs and agonists (e.g., follicle stimulating hormone, growth hormone, adrenocorticotropic hormone, and luteinizing hormone releasing hormone (LHRH)), vaccines (e.g., tumoral, bacterial and viral antigens), antigens, blood coagulation factors, growth factors (NGF and EGF), gastrin, GRH, antibacterial peptides such as defensin, enkephalins, bradykinins, calcitonin and muteins, analogs, truncation, deletion and substitution variants and pharmaceutically acceptable salts of all the foregoing. Other active agents include, but are not limited to somatostatin, testosterone, progesterone, estradiol, nicotine, fentanyl, norethisterone, clonidine, scopolamine, salicylate, cromolyn sodium, salmeterol, albuterol, epinephrine, L-dopa, diazepam, trospium, iloprost, formoterol and budesonide.

HSH is a generic term for various hydrogenated syrups which are also known as "sugar alcohols", "polyhydric alcohols" or "polyols". HSHs are ubiquitous dietary components. They are used as sweeteners, viscosity agents, bodying agents, humectants, crystallization modifiers, and rehydration aids in the food and pharmaceutical industries.

HSHs are derived from such common food substances as maltodextrins, glucose, syrups and maltose syrups. HSH molecules have the chemical structure $(G)_nS$ where G is glucose and S is sorbitol, and n is an integer greater than or equal to zero. Sorbitol $(G)_0S$ is formed by the reduction of glucose, changing the aldehyde to a hydroxyl group. Maltitol $(G)_1S$ is formed by the reduction of maltose, a dimer of glucose, and maltotriotol $(G)_2S$ is composed of two glucose units and a sorbitol moiety. Other higher order polyols contain three or more molecules of glucose and a sorbitol moiety. HSHs that do not contain a specific polyol as the majority component are referred to by the general term "hydrogenated starch hydrosylate".

HSHs are typically prepared by the hydrolysis or partial hydrolysis of starch (such as corn, wheat or potato starch) followed by hydrogenation of the hydrolysis product at high temperature under pressure. Starch is a polymer of repeating glucose units that are linked by glycosidic bonds. Hydrolysis breaks the glycosidic bonds, yielding a heterogeneous mixture of shorter-chain glucose monomers, oliogomers and polymers. The degree of hydrolysis (quantified as DE, or dextrose equivalents) dictates the fraction of glucose monomer present in the solution, which is in turn dictated by the method of hydrolysis (acid hydrolysis, heat or enzymatic digestion). By varying the conditions and extent of hydrolysis, various mono-, di, oligo-, and polymeric hydrogenated saccharides can be obtained. Complete hydrolysis would reduce all higher-order saccharides to glucose monomers (dextrose), a theoretical DE of 1000. Hydrogenation of high DE solution results in a greater proportion of monomeric (sorbitol) and oligomeric polyols in the final product. The grade of HSH is determined by the ratios of maltitol, sorbitol and other higher-order polyols or polysaccharides.

Polyalditol is the preferred HSH of the invention. Polyalditol is a pharmaceutical-grade form of HSH comprising approximately 1% sorbitol, 3.5% maltitol, and 95.5% higher order polyols.

In one embodiment, at least one HSH is present in the biocompatible particles of the invention in an amount of at least 5% by weight. Preferably, the HSH is present in the particles in an amount ranging from about 50% to about 95% by weight. In a preferred embodiment the HSH is polyalditol.

In one embodiment, a buffering agent is present in the particles in an amount of at least 1% to about 50% by weight. In one embodiment, the buffering agent is present in an amount ranging from about 1% to about 25% by weight. Examples of buffering agents which can be employed include, but are not limited to: sodium phosphate, sodium acetate, sodium carbonate, citrate, glycylglycine, histidine, HEPES, arginine, TRIS, glycine and sodium citrate or mixtures thereof. In a preferred embodiment the buffering agent is a hydroxytricarboxylic acid or a salt thereof, such as citric acid or a citrate salt, such as sodium citrate.

The particles suitable for use in the invention can further comprise an amino acid or salt thereof. Examples of amino acids which can be employed include, but are not limited to: glycine, proline, alanine, cysteine, methionine, valine, leucine, tyrosine, isoleucine, phenylalanine and tryptophan. In a preferred embodiment the amino acid is hydrophobic. Suitable hydrophobic amino acids, include but are not limited to, leucine, isoleucine, alanine, valine, phenylalanine, glycine and tryptophan. Combinations of hydrophobic amino acids or combinations of amino acids wherein the overall combination is hydrophobic can also be employed. In a preferred embodiment, the amino acid is leucine.

The amino acid, preferably leucine, can be present in the particles of the invention in an amount from about 1% to about 91 weight %. In one embodiment the amino acid, preferably leucine, can be present in the particles in an amount ranging from about 5 to about 60 weight percent and preferably in an amount ranging from about 5 to about 30 weight percent. In another embodiment, the particles comprise the amino acid, preferably leucine, in an amount of at least 46 weight percent.

In a further embodiment, the particles can also include other materials such as, for example, buffer salts, dextran, polysaccharides, lactose, trehalose, cyclodextrins, proteins, peptides, polypeptides, fatty acids, fatty acid esters, inorganic compounds, and phosphates.

A preferred formulation of the invention comprises about 1% to about 10% by weight of parathyroid hormone or fragment thereof, about 65% to about 95% by weight of polyalditol, about 1% to about 25% by weight of sodium citrate. Another preferred composition comprises about 4.7% by weight of parathyroid hormone or fragment thereof, about 80% by weight of polyalditol, and about 15.3% by weight of sodium citrate.

Another preferred formulation of the invention comprises budesonide and an HSH, preferably polyalditol. Optionally, the formulation further comprises a buffering agent, such as a hydroxytricarboxylic acid including citric acid or a salt thereof. The formulation can further comprise an amino acid. A particularly preferred formulation of the invention comprises about 1% to about 10% by weight of budesonide, about 65% to about 99% by weight of polyalditol and about 0% to about 25% by weight of sodium citrate.

Methods of Treatment and Administration

The method of the invention includes delivering to the pulmonary system an effective amount of a medicament such as, for example, a therapeutic, prophylactic or diagnostic agent. As used herein, the term "effective amount" means the amount needed of a therapeutic, prophylactic or diagnostic agent to achieve the desired therapeutic or diagnostic effect or efficacy e.g, in the case of parathyroid hormones and its analogs, to treat a condition characterized by abnormal levels of parathyroid hormone.

In a preferred embodiment of the invention, the bioactive agent is parathyroid hormone or a fragment thereof. Parathyroid hormone is the most important endocrine regulator of calcium and phosphorus concentration in extracellular fluid. This hormone is secreted from cells of the parathyroid glands and finds its major target cells in bone and kidney. Another hormone, parathyroid hormone-related protein, binds to the same receptor as parathyroid hormone and has major effects on development. Like most other protein hormones, parathyroid hormone is synthesized as a preprohormone. After intracellular processing, the mature hormone is packaged within the Golgi into secretory vesicles, the secreted into blood by exocytosis. Endogenous parathyroid hormone is secreted as a linear protein of 84 amino acids.

Parathyroid hormone functions by stimulating at least three processes. First, PTH mobilizes calcium from the bone. Although the mechanisms remain obscure, a well-documented effect of parathyroid hormone is to stimulate osteoclasts to reabsorb bone mineral, liberating calcium into blood. Second, PTH enhances absorption of calcium from the small intestines. Facilitating calcium absorption from the small intestine would clearly serve to elevate blood levels of calcium. Parathyroid hormone stimulates this process, but indirectly by stimulating production of the active form of vitamin D in the kidney. Vitamin D induces synthesis of a calcium-binding protein in intestinal epithelial cells that facilitates efficient absorption of calcium into blood. Third, PTH suppresses calcium loss in urine. That is, in addition to stimulating fluxes of calcium into blood from bone and intestine, parathyroid hormone puts a brake on excretion of calcium in urine, thus conserving calcium in blood. This effect is mediated by stimulating tubular reabsorption of calcium. Another effect of parathyroid hormone on the kidney is to stimulate loss of phosphate ions in urine (Colorado State University hypertext for biomedical science website). Thus, PTH (1) increases the calcium and phosphorus release from bone, (2) decreases the loss of calcium; (3) increases the loss of phosphorus in the urine; and (4) increases the activation of 25-hydroxy vitamin D to 1,25-dihydroxy vitamin D in the kidneys. Secretion of PTH is regulated by the level of calcium in the blood. Low serum calcium causes increased PTH to be secreted, whereas increased serum calcium inhibits PTH release. Typical normal values are 10-55 pg/ml (pg/ml=picograms per milliliter.) Greater-than-normal levels of PTH may be associated with (1) chronic renal failure; (2) hyperparathyroidism; (3) malabsorption syndrome (inadequate absorption of nutrients in the intestinal tract); (4) osteomalacia in adults; (5) rickets in children; and (6) Vitamin D deficiency. Lower-than-normal levels may be associated with (1) autoimmune destruction of the parathyroid gland, (2) hypomagnesemia; (3) hypoparathyroidism; (4) metastatic bone tumor; (5) milk-alkali syndrome (excessive calcium ingestion); (6) sarcoidosis; and (7) vitamin D intoxication. There is no doubt that chronic secretion or continuous infusion of parathyroid hormone leads to decalcification of bone and loss of bone mass. However, in certain situations, treatment with parathyroid hormone can actually stimulate an increase in bone mass and bone strength. It has been found that this seemingly paradoxical effect occurs when the hormone is administered in pulses (e.g., by once daily injection), and such treatment appears to be an effective therapy for diseases such as osteoporosis. Thus, PTH is useful for the treatment of subjects with abnormal levels of parathyroid hormone.

In another preferred embodiment of the invention, the active agent is budesonide, a glucocorticoid steroid that is used for the treatment of a variety of inflammatory disorders, including asthma and rhinitis. Budesonide is available in several dosage forms, including a formulation for pulmonary delivery marketed under the name Pulmicort® (AstraZeneca), which includes micronized budesonide and lactose and is administered via a nebulizer. The current invention provides inhaleable budesonide formulations that can be administered via a dry powder inhaler and exhibit significant stability, as shown in Example 3. The budesonide formulations of the invention can be used to treat any inflammatory condition, including those conditions for which budesonide is known to be effective, including asthma, allergic or infectious rhinitis, nasal polypsys, and inflammatory bowel disease.

The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations (e.g., by means of an appropriate, conventional pharmacological protocol). For example, effective amounts of the therapeutic, prophylactic or diagnostic agent range from about 0.1 milligrams (mg) to about 100 mg. In another embodiment, at least 5 milligram of a therapeutic, prophylactic or diagnostic agent is delivered by administering, in a single breath, to a subject's respiratory tract the biocompatible particles enclosed in the receptacle. Preferably at least 5 milligrams of therapeutic, prophylactic or diagnostic agent is delivered to a subject's respiratory tract. Amounts of drug as high as 15, 20, 25, 30, 35, 40 or 50 milligrams can be delivered.

The terms "treating", "treatment" and the like are used herein to mean affecting a subject, tissue or cell to obtain a desired pharmacologic and/or physiologic effect. The effect may be prophylactic in terms of completely or partially preventing a a disease or other undesirable condition, for example, conditions characterized by abnormal levels of parathyroid hormone as described above.

The term "subject" or "patient" as used herein refers to any animal having a disease or condition which requires treatment with a pharmaceutically active agent e.g., a therapeutic, prophylactic or diagnostic agent, in particular parathyroid hormone or a fragment thereof. The subject may be a mammal, preferably a human, or may be a non-human primate or non-primates such as used in animal model testing.

The invention is also related to methods for administering to the pulmonary system a therapeutic dose of the medicament in a small number of steps, and preferably in a single, breath-activated step. The invention also is related to methods of delivering a therapeutic dose of a therapeutic, prophylactic or diagnostic agent. The invention also includes administering the biocompatible particles from a receptacle having, holding, containing, storing or enclosing a mass of particles, to a subject's respiratory tract.

In a preferred embodiment, the receptacle is used in a dry powder inhaler. Examples of dry powder inhalers that can be employed in the methods of the invention include but are not limited to the inhalers disclosed is U.S. Pat. Nos. 4,995,385 and 4,069,819, the SPINHALER®. (Fisons, Loughborough, U.K.), ROTAHALER®. (Glaxo-Wellcome, Research Triangle Technology Park, N.C.), FLOWCAPS®. (Hovione, Loures, Portugal), INHALATOR®. (Boehringer-Ingelheim, Germany), and the AEROLIZER®. (Novartis, Switzerland), the Diskhaler (Glaxo-Wellcome, RTP, NC) and others known to those skilled in the art.

In one embodiment, at least 80% of the mass of the biocompatible particles stored in the inhaler receptacle is delivered to a subject's respiratory system in a single, breath-activated step. As used herein, the term "receptacle" includes but is not limited to, for example, a capsule, blister, film covered container well, chamber and other suitable means of storing a powder in an inhalation device known to those skilled in the art.

In one embodiment, the volume of the receptacle is at least about 0.37 cm$^3$. In another embodiment, the volume of the receptacle is at least about 0.48 cm$^3$. In yet another embodiment, are receptacles having a volume of at least about 0.67 cm$^3$ or 0.95 cm$^3$. In one embodiment of the invention, the receptacle is a capsule designated with a capsule size 2, 1, 0, 00 or 000. Suitable capsules can be obtained, for example, from Shionogi (Rockville, Md.). Blisters can be obtained, for example, from Hueck Foils, (Wall, N.J.)

The receptacle encloses or stores particles, also referred to herein as powders. The receptacle is filled with particles, as known in the art. For example, vacuum filling or tamping technologies may be used. Generally, filling the receptacle with powder can be carried out by methods known in the art. In one embodiment of the invention, the article or powder enclosed or stored in the receptacle have a mass of at least about 0.1 milligram to at least about 20 milligrams. In one embodiment, the powder enclosed or stored in the receptacle is present in an amount of at least 0.1, 0.3, 0.6, 0.9, 1, 3, 5, 7, 10, 13, 15, 17, 20, 23, 25, 27, or 30 milligrams.

Delivery to the pulmonary system of particles in a single, breath-actuated step is enhanced by employing particles which are dispersed at relatively low energies, such as, for example, at energies typically supplied by a subject's inhalation. Such energies are referred to herein as "low" As used herein, "low energy administration" refers to administration wherein the energy applied to disperse and/or inhale the particles is in the range typically supplied by a subject during inhaling.

The invention is also related to methods for efficiently delivering powder particles to the pulmonary system. For example, but not limited to, at least about 70% or at least about 80% of the nominal powder dose is actually delivered. As used herein, the term "nominal powder dose" is the total amount of powder held in a receptacle, such as employed in an inhalation device. As used herein, the term nominal drug dose is the total amount of medicament contained in the nominal amount of powder. The nominal powder dose is related to the nominal drug dose by the load percent of drug in the powder.

Properties of the particles enable delivery to patients with highly compromised lungs where other particles prove ineffective for those lacking the capacity to strongly inhale, such as young patients, old patients, infirm patients, or patients with asthma or other breathing difficulties. Further, patients suffering from a combination of ailments may simply lack the ability to sufficiently inhale. Thus, using the methods and particles for the invention, even a weak inhalation is sufficient to deliver the desired dose.

The invention also features a kit comprising at least two receptacles, each receptacle containing a different amount of dry powder therapeutic, prophylactic or diagnostic agents, suitable for inhalation. The powder can be, but is not limited to any such dry powder parathyroid hormone or fragment thereof as described herein. In addition, the invention also features a kit comprising two or more receptacles comprising two or more unit dosages comprising particles comprising the therapeutic, prophylactic or diagnostic agent formulations described herein. The kits may also contain instructions for the use of the reagents in the kits (e.g., the receptacles containing the formulation). Through the use of such kits, accurate dosing can be accomplished.

The kits described herein can be used to deliver a therapeutic, prophylactic or diagnostic agent, for example, parathyroid hormone or a fragment thereof, to a subject in need of the therapeutic, prophylactic or diagnostic agent. When the therapeutic, prophylactic or diagnostic agent is parathyroid hormone, the dose administered to the subject can be altered, for example, by a patient or by a medical provider, by increasing or decreasing the number of receptacles (e.g., capsules) of parathyroid hormone containing particles, thereby increasing or decreasing the unit dosage of the parathyroid hormone. When a patient is in need of a higher dose of parathyroid hormone than usual, that patient can administer to himself or herself additional receptacles, or a different combination of receptacles, so that the dose of parathyroid hormone or a fragment thereof is increased to the desired amount. Conversely, when a patient needs less parathyroid hormone or a fragment thereof, the patient can administer to himself or herself fewer receptacles, or a different combination of receptacles, such that the dose is decreased to the desired amount. The kits may also contain instructions for the use of the reagents in the kits (e.g., the receptacles containing the formulation). Through the use of such kits, accurate dosing can be accomplished.

Administration of Biocompatible Particles

Particles of the invention are suitable for delivering a therapeutic, prophylactic or diagnostic agent to the pulmonary system. "Pulmonary delivery," as that term is used herein refers to delivery to the respiratory tract. Pulmonary delivery is generally the result of oral inhalation by the patient. The "respiratory tract," as defined herein, encompasses the upper airways, including the oropharynx and larynx, followed by the lower airways, which include the trachea followed by bifurcations into the bronchi and bronchioli (e.g., terminal and respiratory). The upper and lower airways are called the conducting airways. The terminal bronchioli then divide into respiratory bronchioli which then lead to the ultimate respiratory zone, namely, the alveoli, or deep lung. The deep lung, or alveoli, are typically the desired target of inhaled therapeutic formulations for systemic drug delivery. In one embodiment of the invention, most of the mass of particles deposit in the deep lung or alveoli. In another embodiment of the invention, delivery is primarily to the central airways. In other embodiments, delivery is to the upper airways.

The particles of the invention can be administered as part of a pharmaceutical formulation or in combination with other therapies be they oral, pulmonary, by injection or other mode of administration. As described herein, particularly useful pulmonary formulations are spray dried dry powder particles having physical characteristics characterized by a fine particle fraction (FPF), geometric and aerodynamic dimensions and by other properties which favor target lung deposition and are formulated to optimize release and bioavailability profiles, as further described below. As used herein, the term "fine particle fraction" of a collection of particles refers to the fraction by weight, typically expressed as weight percent, of the total powder which is present as particles of aerodynamic diameter less than 3.3 µm.

In one embodiment, the FPF of the formulations of the invention is at least about 20%. For example, the FPF of the formulations can be at least about 20% or 30% or 40% or 50%, or 60, or 70%, or 80%, or 90%.

The FPF of the particles of the invention can measured in several ways. In one method of measuring FPF, the gravimetric fine particle fractions as a percentage of the total powder (FPF$_{TP}$<3.3 μm) were obtained gravimetrically at a flow rate of 28.3 L/min using stages 0, 2, and 3 of an Andersen Cascade Impactor (ACI) with effective cut-off diameters of 9.0, 4.7, and 3.3 μm, respectively. Filters were placed on the impaction plate below stage 3 and on the filter stage of the ACI. A flow meter, timing device, and vacuum pump were connected to the impactor and the flow rate was adjusted to 28.3 L/min. The inhaler was then actuated and powder was emitted, with a total volume of 2 L of air drawn through the inhaler and impactor. The difference in the filter weights before and after dose emission was used to calculate the gravimetric fine particle fractions.

Another method of measuring the aerodynamic size distribution is with a Next Generation Impactor (NGI). The NGI operates on similar principles of inertial impaction as the ACI. The NGI consists of seven stages and is calibrated at flow rates of 30, 60, and 100 LPM. In contrast to the ACI, for which the impactor stages are stacked, the stages of the NGI are all in one plane. Collection cups are used to collect the particles below each stage of the NGI.

Another method for measuring the size distribution of airborne particles is the Multi-stage liquid Impinger (MSLI). The Multi-stage liquid Impinger (MSLI) operates on the same principles as the ACI and NGI, but with five stages in the MSLI. Additionally, instead of each stage consisting of a solid plate or collection cup, each MSLI stage consists of a wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

In one preferred embodiment, the particles have a tap density of less than about 0.4 g/cm$^3$. Particles which have a tap density of less than about 0.4 g/cm$^3$ (e.g., 0.4 g/cm$^3$) are referred to herein as "aerodynamically light particles". For example, the particles have a tap density less than about 0.3 g/cm$^3$, or a tap density less than about 0.2 g/cm$^3$, a tap density less than about 0.1 g/cm$^3$. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

The particles of the invention have a preferred size, e.g., a volume median geometric diameter (VMGD) of at least about 1 micron. In one embodiment, the VMGD is from about 1 μm to 30 μm, or any subrange encompassed by about 1 μm to 30 μm, for example, but not limited to, from about 5 μm to about 30 μm, or from about 10 μm to 30 μm. For example, the particles have a VMGD ranging from about 1 μm to 10 μm, or from about 3 μm to 7 μm, or from about 5 μm to 15 μm or from about 9 μm to about 30 μm. The particles have a mean diameter, mass mean diameter (MMD), a mass median envelope diameter (MMED) or a mass median geometric diameter (MMGD) of at least 1 μm, for example, 5 μm or near to or greater than about 10 μm. For example, the particles have a MMGD greater than about 1 μm and ranging to about 30 μm, or any subrange encompassed by about 1 μm to 30 μm, for example, but not limited to, from about 5 μm to 30 μm or from about 10 μm to about 30 μm. A person skilled in the art can use the term "volume mean geometric diameter" and "volume median geometric diameter" interchangeably without regard to their statistical meaning.

The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 μm and about 5 μm or any subrange encompassed between about 1 μm and about 5 μm. For example, but not limited to, the MMAD is between about 1 μm and about 3 μm, or the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid Impinger (MSLI).

The aerodynamic diameter, $d_{aer}$, can be predicted from the equation:

$$d_{aer}=d_g\sqrt{\rho_{tap}}$$

where $d_g$ is the geometric diameter, for example the MMGD, and ρ is the powder density.

Particles which have a tap density less than about 0.4 g/cm$^3$, median diameters of at least about 1 μm, for example, at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials,* 7: 61-66 (1986); Krenis, L. J. and Strauss, B., *Proc. Soc. Exp. Med.,* 107: 748-750 (1961); and Rudt, S. and Muller, R. H., *J. Contr. Rel.,* 22: 263-272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having an aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, (Gonda, I., "Physico-chemical principles in aerosol delivery,"
In Topics in Pharmaceutical Sciences 1991 (eds. D. J. A. Crommelin and K. K. Midha), pp. 95-117, Stuttgart: Medpharm Scientific Publishers, 1992)), by the formula:

$$d_{aer} = d\sqrt{\rho}$$

where the envelope mass p is in units of g/cm³. Maximal deposition of monodispersed aerosol particles in the alveolar region of the human lung (about 60%) occurs for an aerodynamic diameter of approximately $d_{aer}$=3 μm (Heyder, J. et al., *J. Aerosol Sci.*, 17:811-825 (1986)). Due to their small envelope mass density, the actual diameter d of aerodynamically light particles comprising a monodisperse inhaled powder that will exhibit maximum deep-lung deposition is:

$$d = 3/\sqrt{\rho}\mu m \text{ (where } \rho \text{ is in g/cm}^3\text{);}$$

where d is always greater than 3 μm. For example, aerodynamically light particles that display an envelope mass density, ρ, of 0.1 g/cm³, will exhibit a maximum deposition for particles having envelope diameters as large as 9.5 μm. The increased particle size diminishes interparticle adhesion forces. Visser, J., *Powder Technology*, 58:1-10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

Administration of particles to the respiratory system can be by means such as known in the art. For example, particles are delivered from an inhalation device such as a dry powder inhaler (DPI). Metered-dose-inhalers (MDI), nebulizers or instillation techniques also can be employed. Preferably, the particles are administered as a dry powder via a dry powder inhaler.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848 issued Dec. 7, 1999 to Patton, et al. Other examples include, but are not limited to, the SPINHALER®. (Fisons, Loughborough, U.K.), ROTAHALER®. (Glaxo-Wellcome, Research Triangle Technology Park, N.C.), FLOWCAPS®. (Hovione, Loures, Portugal), INHALATOR®. (Boehringer-Ingelheim, Germany), and the AEROLIZER®. (Novartis, Switzerland), the diskhaler (Glaxo-Wellcome, RTP, N.C.) and others, such as known to those skilled in the art. In one embodiment, the inhaler employed is described in U.S. Pat. No. 6,766,799, issued Jul. 27, 2004 to Edwards, et al., and in U.S. Pat. No. 6,732,732, issued May 11, 2004 to Edwards, et al. The entire contents of these applications are incorporated by reference herein.

Spray Drying

The invention also is related to producing particles that have compositions and aerodynamic properties described above. In a preferred embodiment, the particles of the invention are produced as a dry powder composition by spray drying. Generally, spray-drying techniques are described, for example, by K. Masters In "Spray Drying Handbook", John Wiley & Sons, New York, 1984. In this method, first and second components can be prepared, one or both of which comprises a therapeutic, prophylactic or diagnostic agent. For example, the first component comprises an active agent, e.g., a parathyroid hormone dissolved in the aqueous phase, and the second component, comprising excipients e.g., hydroxytricarboxylic acid or a salt thereof and an HSH, is dissolved in either the aqueous or organic phase depending on solubility, where the organic solvent is typically ethanol, or an ethanol/water mixture. The first and second components can be combined either directly or through a static mixer to form a combination. The combination can be atomized to produce droplets that are dried to form dry particles. In one aspect of this method, the atomizing step can be performed immediately after the components are combined in the static mixer.

Suitable organic solvents that can be present in the mixture being spray dried include, but are not limited to, alcohols, for example, ethanol, methanol, propanol, isopropanol, butanols, and others. Other organic solvents include, but are not limited to, perfluorocarbons, dichloromethane, chloroform, ether, ethyl acetate, methyl tert-butyl ether and others. Aqueous solvents that can be present in the feed mixture include water and buffered solutions. Both organic and aqueous solvents can be present in the spray-drying mixture fed to the spray dryer. In one embodiment, an ethanol/water solvent is preferred with the ethanol:water ratio ranging from about 20:80 to about 80:20. The mixture can have an acidic or alkaline pH. Preferably, the amount of organic solvent can be present in the co-solvent in an amount ranging from about 30 to about 90% by volume. In a more preferred embodiment, the organic solvent is present in the co-solvent in an amount ranging from about 45 to about 60% by volume. Optionally, a pH buffer can be included. Preferably, the pH can range from about 3 to about 10, for example, from about 6 to about 8.

An apparatus for preparing a dry powder composition is provided. The apparatus includes a static mixer (e.g., a static mixer as more fully described in U.S. Pat. No. 4,511,258, the entirety of which is incorporated herein by reference, or other suitable static mixers such as, but not limited to, model 1/4-21, made by Koflo Corporation) having an inlet end and an outlet end. The static mixer is operative to combine an aqueous component with an organic component to form a combination. Means are provided for transporting the aqueous component and the organic component to the inlet end of the static mixer. An atomizer is in fluid communication with the outlet end of the static mixer to atomize the combination into droplets. Heated drying gas is introduced to the spray dryer to provide energy for droplet evaporation and particle drying. The atomizer can be a rotary atomizer. Such a rotary atomizer may be vaneless, or may contain a plurality of vanes. Alternatively the nozzle can be a two-fluid mixing nozzle. Such a two-fluid mixing nozzle may be an internal mixing nozzle or an external mixing nozzle. Alternatively the nozzle can be a pressure nozzle or an ultrasonic nozzle. The means for transporting the aqueous and organic components can be two or more separate pumps, or a single pump. The apparatus can also include a geometric particle sizer that determines a geometric size distribution of the dry particles, and an aerodynamic particle sizer that determines an aerodynamic diameter of the dry particles.

The aqueous solvent and the organic solvent that make up the active agent solution are combined either directly or through a static mixer. The active agent solution is then transferred to a two fluid atomizer nozzle (e.g., within a spray dryer) at a flow rate of about 5 to 75 g/min (mass) and about 6 to 80 ml/min (volumetric). For example, the active agent solution is transferred to the spray drier at a flow rate of 28 g/min and 30 ml/min. The 2-fluid nozzle disperses the liquid solution into a spray of fine droplets which come into contact with a heated drying air or heated drying gas (e.g., nitrogen) under the following conditions:

The pressure within the nozzle is from about 10 psi to 100 psi; an atomization liquid flow rate of about 13 to 67 g/min (mass) and a liquid feed of 10 to 70 ml/min (volumetric); an atomization gas flow rate of 10 to 100 g/min; an atomization gas to liquid ratio from about 1:3 to 6:1; the drying medium, heated air or gas has a feed rate of about 80 to 110 kg/hr an inlet temperature from about 90° C. to 150° C.; an outlet temperature from about 40° C. to 71° C. For example, but not limited to, the pressure within the nozzle is set at 75 psi; the heated gas has a feed rate of 95 kg/hr; and an atomizer gas flow rate of 22.5 g/min and a liquid feed rate of 70 ml/min; the gas to liquid ratio is 1:3; the inlet temperature is 121° C.; the outlet temperature is 48° C.; the baghouse temperature is 43° C.

The contact between the heated nitrogen and the liquid droplets causes the liquid to evaporate and porous particles to result. The resulting gas-solid stream is fed to the product filter, which retains the fine solid particles and allows that hot gas stream, containing the drying gas, evaporated water and ethanol, to pass. The formulation and spray drying parameters are manipulated to obtain particles with desirable physical and chemical characteristics. Other spray-drying techniques are well known to those skilled in the art. An example of a suitable spray dryer using two-fluid atomization includes the Mobile Niro spray dryer, manufactured by Niro, Denmark. The hot gas can be, for example, air, nitrogen, carbon dioxide or argon.

The biocompatible particles of the invention are obtained by spray drying using an inlet temperature between about 90° C. and about 150° C. and an outlet temperature between about 40° C. and about 85° C.

The biocompatible particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

The invention is further illustrated by the following non-limiting examples.

EXAMPLES

Introduction

The inventors have previously demonstrated that maltodextrin of various molecular weights (or dextrose equivalents) spray-dries well in formulations using a variety of processing conditions. Maltodextrin powders were produced that have low tapped densities (<0.4 g/mL) and large median geometric particle sizes (>5 µm), that disperse well, and demonstrate good aerodynamic properties. Maltodextrin powders have a relatively low hygroscopicity and are stable up to 75% RH (depending upon molecular weight) and are additionally thermally stable at elevated temperatures (up to 50° C.). However, maltodextrin contains carbonyl groups which can act as a reducing sugar and potentially participate in the Maillard reaction with proteins and/or peptides.

Polyalditol is similar in structure and properties to maltodextrin with the exception of hydrogenation, which converts it to a sugar alcohol, making it non-reactive with proteins and peptides susceptible to the Maillard reaction. Based on this information the rationale for using polyalditol is that it spray dries similarly to maltodextrin in accordance with the invention, resulting in powders with good physical stability and aerodynamic properties, but is less reactive with proteins and peptides in terms of chemical stability. This and other unexpected advantages of the polyalditol-containing formulations of the invention are described in the following studies.

EXPERIMENTAL PROCEDURES

Materials and Methods

Materials

Teriparatide has an identical sequence to the 34 N-terminal amino acids of human parathyroid hormone (PTH) and has the same binding affinity for the surface receptors that mediate its biological activity. Teriparatide is manufactured by Eli Lilly and Company using a recombinant DNA technology. Teriparatide used in the following experiments was obtained through Lilly. Lactose, trehalose, citric acid, sodium citrate dihydrate, maltodextrin, calcium chloride, calcium ascorbate, calcium hydroxide and sucrose were purchased from Spectrum Chemical. Dipalmitoyl phosphatidylcholine (DPPC) was obtained from Genzyme Corporation. Dipalmitoyl phosphatidylethanolamine (DPPE), dimyristoyl phosphatidylethanolamine (DMPE), and distearoyl phosphatidylcholine (DSPC) were obtained from Avanti Polar Lipids. Innovatol PD60—polyalditol was purchased from Grain Processing Corporation. Water for Irrigation was purchased from B. Braun. Water for Injection was manufactured at Alkermes. Ethanol was purchased from Pharmco and Aaper Alcohol & Chemical Co. Size 2 HPMC capsules were manufactured by Shionogi and obtained from Alkermes. Inhalers were obtained from Alkermes. Budesonide was obtained from Spectrum Chemicals.

Methods

Spray Drying Process

Teripearatide inhalation powders (TIP) and budesonide inhalation powders are produced by spray drying solutions of dissolved raw materials. The aqueous solution potentially contains the water soluble excipient(s) and drug(s) if applicable, and the organic solution contains the solvent, organic soluble excipients (phospholipids), and drug(s) if applicable. The aqueous and organic phases can be separately pumped to an ISG (interfacial surface generator) static mixer, where they are combined. The flow rates of the individual phases are monitored via flowmeters prior to static mixing. Based on formulation and solubility requirements, the in-line feed solutions can be heated to control for temperature. The combined solution is pumped to an atomizer at the top of a size-1 Niro spray dryer. The solution is atomized using a 2-fluid nozzle. The nitrogen gas atomizes the liquid stream, breaking it into small droplets as it exits the 2-fluid atomizer.

Nitrogen drying gas is heated to the target temperature and sent into the drying chamber through a disperser surrounding the atomizer at the top of the dryer. The atomized liquid droplet is then dried with the drying gas under vacuum in the spray drying chamber. The dried powder exits the bottom of the spray dryer and is carried to the product filter housing by the drying gas, where it is collected on a product filter bag. Following spray drying, the filter bag is pulsed with nitrogen, and the filter housing is air hammered. The powder falls into the collection vessel at the bottom of the product filter housing and the collection vessel containing the powder is removed from the system.

The bulk powder is then transferred at ambient temperature to an RH (relative humidity) controlled glove box, scraped into an amber jar, and stored at refrigerated conditions. All runs were completed on a size 1 Niro spray dryer with a two-fluid atomizer and baghouse filter for powder collection. The atomization gas rate was maintained between 10 and 100 g/min. Nozzle back-pressure was maintained between 10 and 100 psig, and the atomizer gas/feed rate ratio was maintained between 0.2 and 2.0. The outlet temperature was maintained between 50° C. and 120° C. The drying gas rate was maintained between 50 and 150 kg/hr. Total liquid feed rate for all runs was between 10 and 100 mL/min for all runs.

Volume Median Geometric Particle Size

Geometric particle size of bulk powder is determined using a Fraunhofer laser diffraction technique. The equipment consists of a HELOS diffractometer (Sympatec, Inc.) and a RODOS dispersion system to control the primary and depression pressures. The dispersed particles are drawn through a laser beam where the resulting diffracted light pattern is collected by detectors. The diffraction pattern is then translated into a volume-based particle size distribution. The monitored results are the volume median geometric diameter (VMGD).

Fine Particle Fraction (ACI-3)

The fine particle fraction of the total dose (FPF <3.3 μm (% TP)) is obtained gravimetrically at a flow rate of 28.3 LPM, using a 3-stage Andersen Cascade Impactor. The screens may be coated with a solvent, such as methanol, and placed on impaction plates below each stage to minimize particle bounce. The effective cut-off diameter of the stages are 9.0 μm, 4.7 μm, and 3.3 μm. A flow meter, flow controller, and pump are connected to the impactor and the flow rate is adjusted to target. The capsule, with fill weight of between 2 and 20 mg, is punctured within the inhaler, and the flow is turned on for 4.2 seconds (target 2.0 L total volume). The filter is weighed before and after powder emission to determine the fine particle fraction of the total dose less than 3.3 μm (% TP).

Emitted Powder (EP) using Gravimetric Analysis

The dose emitted from the inhaler is obtained gravimetrically at various flow rates and volumes, using an inlet cone and filter assembly connected to a flow meter, flow controller, and pump. The duration and rate of flow are adjusted using the flow controller, with durations that correspond to specific volumes of air. For each determination, the capsule is punctured within the inhaler; the inhaler is inserted into an adapter on the cone and filter assembly, and the flow turned on for the required duration. The filter is removed and weighed to determine the mass of powder emitted. Multiple determinations are made for each set of flow conditions. An inhaler is used with flow parameters of 28.3 LPM flow rate and 2.0 L volume, using a fill weight of between 2 and 20 mg in size 2 HPMC capsules.

Emitted Geometric Particle Size

The emitted geometric particle size from the inhaler was measured according to Alkermes SOP 110-00640 ver.02 that describes the method for using the IHAv2 and the HELOS laser diffractometer to obtain the geometric particle size distribution of the emitted powder. XLP inhalers were used at 28.3 LPM/2.0 L volume, using a fill weight of 6±0.5 mg in size 2 HPMC capsules.

Tapped Density

The tapped density of bulk powder is determined using a modified version of the USP <616> Bulk Density and Tapped Density method as described in the United States Pharmacopoeia. The modified method uses a smaller powder volume and reports the mean tapped density in g/mL, to two significant figures.

Bulk Powder Temperature and Relative Humidity Studies

The VMGD of the TIP and budesonide formulations was assessed using the volume median geometric particle size method following overnight exposure of approximately 50 mg of bulk powder in opened vials to a range of relative humidity (16, 32, 43, 57, and 75% at ambient temperature) or elevated temperatures (37 and 50° C.) in sealed chambers. The test assessed physical stability (powder agglomeration) to temperature and relative humidity exposure as indicated by the change in VMGD following overnight exposure of the powders to various relative humidities or temperatures.

Water Content

Water content determination was made on a Brinkmann (Metrohm) 756 Karl Fischer coulometer with a 774 oven sample processor using standard methods. A sample weight of 50 mg was used to allow for the lower water contents of the powders.

Chemical Purity and Drug Content

Chemical purity and drug content of the drug products were determined by standard analytical methods as described below.

Teriparatide

PTH purity and drug content for the PTH-containing formulations were determined using the following methods.

Related impurities analysis was performed on a Waters 2695 separations module equipped with a Waters 2487 UV detector. Column was a Zorbax 300-SB C18, 4.6×150 mm, 3.5 μm particle size (Agilent P/N 863973-902). Mobile phase A was 200 mM sodium sulfate buffer prepared by dissolving sodium sulfate in HPLC grade water and adjusting to pH 2.3 using phosphoric acid. Mobile phase B was acetonitrile. The gradient profile is located in Table 1.

TABLE 1

HPLC gradient profile for determination of
impurities in teriparatide formulations.

| Time (min.) | A (%) | B (%) |
|---|---|---|
| 0 | 90 | 10 |
| 5 | 76 | 24 |
| 35 | 74 | 26 |
| 45 | 50 | 50 |

Column temperature was 40° C. Samples were stored at 5° C. Flow rate was 1 mL/min. Injection volume was 50 μL. Samples were prepared in HPLC grade water at a concentration of 250 μg Teriparatide per milliliter of solution.

A reverse phase-HPLC method was used to measure the drug assay/content of TIP. As with the impurities method, HPLC grade water was used to better dissolve samples. Each sample was prepared in triplicate. The sample of interest was added to each set of 3 assay samples 30 min before being run on the HPLC to avoid unnecessary degradation in solution. The drug content reported herein is expressed on a percent dry basis.

Budesonide

For budesonide, drug content and impurity levels are both determined by reverse phase HPLC analysis using a Waters Symmetry C4 3.5 micron, 4.6×150 mm column with gradient elution. The method parameters are shown in Table 2. The gradient profile is shown in Table 3.

TABLE 2

Method parameters for determination of budesonide
and impurity levels in budesonide formulations.

| | |
|---|---|
| Injection volume | 20 μL |
| Run time | 22 min |
| Column Temperature | 30° C. |
| Sample Temperature | 2-8° C. |
| Detection | 245 nm |
| Sample Diluent | 50% Acetonitrile |

TABLE 3

HPLC gradient profile for determination of budesonide
and impurity levels in budesonide formulations.

| Flow rate (mL/min) | Time (min) | Water (%) | Acetonitrile (%) |
|---|---|---|---|
| 1 | 0 | 90 | 10 |
| | 3 | 90 | 10 |
| | 10 | 30 | 70 |
| | 18 | 30 | 70 |

Example 1

Spray Drying TIP Candidates to Understand the Role of Excipients in Chemical and Physical Stability To establish whether the reducing sugars (maltodextrin and lactose) were contributing to the formation of impurities during storage, the impact of formulation and spray drying process conditions on the chemical and physical stability of various spray dried TIP powders was explored. The experiments were designed to study the effect of formulation and spray drying process conditions on the chemical and physical stability of early stage spray dried TIP powders. The key points of the study included: a broad range of DPPC: lactose ratios; the level of sodium citrate in the formulation, sodium phosphate compared to sodium citrate, solution pH, and ethanol concentration. The powders were initially characterized and stored refrigerated prior to the initiation of the stability study. For the stability study, the powders were equilibrated at 20% RH at ambient temperature overnight. Following RH equilibration, the bulk powders were sealed in vials with parafilm and packaged in foil bags. The foil bags were placed in a controlled temperature environment at either 25° C. for testing at time zero, 2 weeks and 4 weeks or at 40° C. for testing at 1 week and 2 weeks.

The ACI-3 and total related impurity results following storage of the various formulations, listed in Table 4, demonstrated several points. Formulations containing either lactose or maltodextrin generated higher levels of impurities than those formulations without a reducing sugar excipient. The lactose formulations produced with high ethanol (≥55%) and all of the maltodextrin formulations had greater than 10% impurities following 1 week of storage at 40° C.; whereas the DPPC/citrate (run 3) and polyalditol (run 15) formulations had the lowest levels of impurities following 1 week of storage at 40° C. The lactose formulation produced with 30% ethanol had an impurity level of 4% after 4 weeks of storage at 25° C.; whereas the same formulation produced with 70% ethanol had an impurity level of 43%. From this data it was concluded that the presence of reducing sugars, especially in formulations with ethanol concentrations of ≥55%, negatively impacted the chemical stability of teriparatide. Additionally, the DPPC/citrate and polyalditol formulations, runs 3 and 15 respectively, were deemed chemically and physically stable when stored at 25° C. and were selected for additional formulation screening studies.

TABLE 4

Impact of Formulation Excipients on Powder Properties and Stability

| | | | Initial Data | | ACI-3 | | | Impurities | | | |
|---|---|---|---|---|---|---|---|---|---|---|---|
| Lot No. | Run | Formulation (ratio) | VMGD @ 1 bar | Tapped Density | Tzero | 1 wk @ 40° C. | 2 wk @ 25° C. | Tzero | 1 wk @ 40° C. | 2 wk @ 40° C. | 2 wk @ 25° C. | 4 wk @ 25° C. |
| 200-00036-122 | 1 | DPPC/Lactose/Citrate/pTH (60/20/15.5/4.5) - 55% EtOH | 10.0 | 0.07 | 35 | 35 | 31 | 2.5 | 14.6 | 21.0 | 4.4 | 5.2 |
| 200-00036-123 | 2 | DPPC/Lactose/Citrate/pTH (60/20/15.5/4.5) - 70% EtOH | 8.2 | 0.19 | 31 | 27 | 33 | 2.6 | 17.6 | 23.6 | 4.6 | 5.5 |
| 200-00036-124 | 3 | DPPC/Citrate/pTH (80/15.5/4.5) - 70% EtOH | 8.2 | 0.21 | 24 | 17 | 29 | 2.1 | 5.4 | 6.7 | 2.1 | 2.7 |

TABLE 4-continued

Impact of Formulation Excipients on Powder Properties and Stability

| | | | Initial Data | | ACI-3 | | | Impurities | | | | |
|---|---|---|---|---|---|---|---|---|---|---|---|---|
| Lot No. | Run | Formulation (ratio) | VMGD @ 1 bar | Tapped Density | Tzero | 1 wk @ 40° C. | 2 wk @ 25° C. | Tzero | 1 wk @ 40° C. | 2 wk @ 40° C. | 2 wk @ 25° C. | 4 wk @ 25° C. |
| 200-00036-125 | 4 | Lactose/Citrate/pTH (80/15.5/4.5) - 70% EtOH | 6.2 | 0.35 | 23 | 21 | n.t. | 16.4 | 76.0 | n.t. | 37.1 | 42.7 |
| 200-00036-126 | 5 | DPPC/Lactose/Citrate/pTH (70/10/15.5/4.5) - 70% EtOH | 6.5 | 0.21 | 32 | 27 | n.t. | 2.2 | 18.2 | n.t. | 4.8 | 6.0 |
| 200-00036-127 | 6 | DPPC/Lactose/Citrate/pTH (40/20/35.5/4.5) - 70% EtOH | 6.6 | 0.25 | 28 | 33 | n.t. | 2.1 | 14.7 | n.t. | 5.7 | 5.0 |
| 200-00036-128 | 7 | DPPC/Lactose/Citrate/pTH (70/20/5.5/4.5) - 70% EtOH | 6.8 | 0.25 | 28 | 20 | n.t. | 2.4 | 17.3 | n.t. | 4.4 | 5.3 |
| 200-00036-129 | 8 | Lactose/Citrate/pTH (80/15.5/4.5) - 30% EtOH | 14.8 | 0.06 | 23 | 24 | 23 | 2.6 | 8.4 | 12.5 | 4.0 | 3.8 |
| 200-00036-130 | 9 | DPPC/Lactose/Phosphate/pTH (60/20/15.5/4.5) - 70% EtOH - pH 7.0 | 7.3 | 0.19 | 28 | 18 | n.t. | 2.3 | 19.8 | n.t. | 5.2 | 6.8 |
| 200-00036-131 | 10 | DPPC/Lactose/Phosphate/pTH (60/20/15.5/4.5) - 70% EtOH - pH 5.5 | 6.3 | 0.25 | 20 | 7 | n.t. | 2.0 | 30.7 | n.t. | 4.2 | 5.3 |
| 200-00036-132 | 11 | DPPC/Lactose/Phosphate/pTH (60/20/15.5/4.5) - 70% EtOH - pH 8.5 | 7.8 | 0.25 | 17 | 10 | n.t. | 4.4 | 28.4 | n.t. | 8.8 | 10.4 |
| 200-00036-133 | 12 | DPPC/Phosphate/pTH (80/15.5/4.5) - 70% EtOH | 8.5 | 0.23 | 25 | −1 | n.t. | 1.8 | 11.1 | n.t. | 2.5 | 3.2 |
| 200-00036-134 | 13 | Maltodextrin M100/Citrate/pTH (88/7.5/4.5) - 45% EtOH | 7.4 | 0.12 | 38 | 34 | n.t. | 2.2 | 14.2 | n.t. | 5.0 | 6.0 |
| 200-00036-135 | 14 | Maltodextrin M100/Citrate/pTH (88/7.5/4.5) - 30% EtOH | 14.4 | 0.05 | 26 | 23 | n.t. | 2.7 | 12.5 | n.t. | 4.9 | 5.9 |
| 200-00036-136 | 15 | Polyalditol PD60/Citrate/pTH (80/15.5/4.5) - 30% EtOH | 14.0 | 0.06 | 23 | 24 | 25 | 1.9 | 2.9 | 3.4 | 2.0 | 2.3 | n.t. denotes not tested

Example 2

Effect of T/RH and Bare Capsule Exposure on TIP Formulations

In this study, the effect of bare capsule exposure to patient in-use temperature and relative humidity conditions of 25° C./75% RH and 30° C./75% RH was evaluated to determine the robustness of these formulation for further development in preparation for Phase I clinical trials. System performance was characterized by emitted powder, Fine Particle Fraction <3.3 µm and water content with bare capsule exposure times of 30 and 60 minutes. Those results were compared to data obtained at standard conditions (25° C./30% RH) with zero minutes of bare capsule exposure. In brief, the dose delivery for the following TIP formulations was assessed:

Polyalditol/Citrate/Teriparatide (80/15.5/4.5)

DPPC/Citrate/Teriparatide (80/15.5/4.5)

DPPC/CaCl$_2$/Citrate/Teriparatide (70/10/15.5/4.5)

DPPC/Sucrose/Citrate/Teriparatide (60/20/15.5/4.5)

The dose delivery results obtained at 30° C./75% RH (representing Zone 4 conditions) for TIP formulations are shown in Table 5. There was no effect of bare capsule exposure up to 30 minutes on the dose delivery at 30° C./75% RH for the polyalditol formulation. The effect of T/RH on the dose delivery for the DPPC/calcium chloride formulation was greater than the polyalditol formulation but less than the DPPC or DPPC/Sucrose formulations. The fine particle fraction results obtained after bare capsule exposure to the T/RH condition (30° C./75% RH) are shown in Table 6. For an exposure time of up to 30 minutes no significant effect was noted to fine particle fraction.

TABLE 5

The emitted powder results obtained at 30° C./75% RH for TIP formulations

| Lot No: | Formulation (ratio) | Exposure Time (min) | Emitted Powder (% TP) Mean | Standard Deviation |
|---|---|---|---|---|
| 200-00036-163 | Polyalditol/Citrate/ Teriparatide (80/15.5/4.5) | Control | 82 | 1 |
| | | 0 | 82 | 2 |
| | | 15 | 78 | 2 |
| | | 30 | 79 | 6 |
| 200-00036-187 | DPPC/CaCl2/Citrate/ Teriparatide (70/10/15.5/4.5) | Control | 81 | 2 |
| | | 0 | 63 | 5 |
| 200-00036-151A | DPPC/Sucrose/Citrate/ Teriparatide (60/20/15.5/4.5) | Control | 82 | 4 |
| | | 0 | 43 | 8 |
| 200-00036-181 | DPPC/Citrate/ Teriparatide (80/15.5/4.5) | 0 | 24 | 3 |
| | | 15 | 24 | 2 |
| | | 30 | 27 | 5 |

TABLE 6

The fine particle fraction results obtained at 30° C./75% RH for TIP formulations

| Lot No: | Formulation (ratio) | Exposure Time (min) | FINE PARTICLE FRACTION (% TP) Mean | Standard Deviation |
|---|---|---|---|---|
| 200-00071-009 | Polyalditol/Citrate/ Teriparatide (80/15.5/4.5) | 0 | 37 | 1 |
| | | 15 | 32 | 4 |
| | | 30 | 30 | 2 |
| | | 60 | 22 | 5 |

Example 3

Preparation and Characterization of Spray-Dried Budesonide/Polyalditol Formulations A series of budesonide/polyalditol formulations were prepared using the general methods described above and the process parameters set forth in Table 7. The resulting particles were characterized to determine the effect of certain formulation and spray drying process conditions on the chemical and physical stability of spray dried budesonide powders. As set forth in Table 7, these formulations varied in terms of budesonide, polyalditol, and sodium citrate content, and process conditions, including solvent composition.

The stability of the following formulations was assessed at 20% relative humidity and either 40° C. or 25° C.
Polyalditol/Budesonide/Sodium Citrate 90/5/5
Polyalditol/Budesonide/Sodium Citrate 65/5/30
Polyalditol/Budesonide 95/5
These formulations were compared to bulk budesonide and spray-dried budesonide. The results, presented in Table 8, show that all of the polyalditol formulations tested were stable over four weeks at 40° C. In fact, the stability of the budesonide in these formulations was similar to that seen for the bulk budesonide and the spray-dried budesonide particles.

While this invention has been particularly shown and described with references to preferred embodiments thereof, it will be understood by those skilled in the art that various changes in form and details may be made therein without departing from the scope of the invention encompassed by the appended claims.

What is claimed is:

1. A dry powder composition for administration to the respiratory system of a patient comprising biocompatible particles wherein the biocompatible particles comprise a therapeutic agent, or any combination thereof; and polyalditol.

2. The composition of claim 1, wherein polvalditol is present in the particles in an amount from about 50% by weight to 95% by weight.

3. The composition of claim 1, further comprising a buffering agent.

4. The composition of claim 3, wherein the buffering agent is sodium phosphate, sodium acetate, sodium carbonate, glycylglycine, histidine, HEPES, arginine, TRIS, glycine or a hydroxytricarboxylic acid or salt thereof.

5. The composition of claim 4 wherein the hydroxytricarboxylic acid is citric acid.

6. The composition of claim 3, wherein the buffering agent is a citrate salt.

TABLE 7

Process parameters for the preparation of polyalditol/budesonide formulations.

| Lot Number | Formulation Ratio | Formulation | Solvent Ratio (EtOH/$H_2O$) | Atom. Gas Rate (g/min) | Formulation Ratio | Nozzle Pressure | Yield (%) | FPF <3.3 mm | Average Tapped Density (g/mL) |
|---|---|---|---|---|---|---|---|---|---|
| 00194-27 | 95/5 | Polyalditol/Budesonide | 35/65 | 30 | 50 | 35 | 7.1 | na | 0.12 |
| 00194-37 | 95/5 | Polyalditol/Budesonide | 35/65 | 35 | 50 | 36-45 | | 23 | 0.14 |
| 00194-51 | 94/5/1 | Polyalditol/Budesonide/Citrate | 45/55 | 34 | 50 | 45 | | 25 | 0.08 |
| 00194-52 | 90/5/5 | Polyalditol/Budesonide/Citrate | 45/55 | 40 | 50 | 55 | 37.6 | 25 | 0.10 |
| 00194-53 | 80/5/15 | Polyalditol/Budesonide/Citrate | 45/55 | 38 | 50 | 52 | 6.2 | 25 | 0.11 |
| 00194-54 | 65/5/30 | Polyalditol/Budesonide/Citrate | 45/55 | 45 | 50 | 62 | 22.9 | 27 | 0.10 |
| 00194-79 | 85/10/5 | Polyalditol/NaCl/Budesonide | 35/65 | 35 | 50 | 43 | 97.3 | | 0.17 |
| 00194-80 | 75/20/5 | Polyalditol/NaCl/Budesonide | 35/65 | 35 | 50 | 44 | 76.7 | | 0.16 |
| 00194-84 | 95/5 | Polyalditol/Budesonide | 20/80 | 28 | 50 | 33-40 | 85.7 | | 0.13 |
| 00194-85 | 95/5 | Polyalditol/Budesonide | 20/80 | 24 | 50 | 39-136 | 64.0 | | 0.05 |
| 00194-86 | 85/10/5 | Polyalditol/Citrate/Budesonide | 20/80 | 26 | 50 | 32-37 | 57.3 | | 0.10 |

TABLE 8

Results of stability testing of budesonide formulations.

| Lot Number | Formulation | Mean Content (%) $T_0$ | Mean Purity (%) $T_0$ | Mean Water Content (%) $T_0$ | Mean Content (%) 2 weeks, 40° C. | Mean Purity (%) 2 weeks, 40° C. | Mean Content (%) 4 weeks, 40° C. | Mean Purity (%) 4 weeks, 40° C. |
|---|---|---|---|---|---|---|---|---|
| 00194-52 | Polyalditol/Budesonide/Citrate | 4.93 | 97.38 | 5.86 | 4.96 | 97.09 | 4.97 | 97.04 |
| 00194-54 | Polyalditol/Budesonide/Citrate | 4.97 | 97.41 | 7.41 | ND | ND | 4.94 | 96.3 |
| 00194-37 | Polyalditol/Budesonide | 5.10 | 98.04 | 5.03 | 5.02 | 98.02 | 5.04 | 97.72 |
| VG0169 | Budesonide (bulk API) | 98.8 | 96.88 | na | 100.19 | 97 | 98.94 | 97 |
| 00197-036-2 | Budesonide, spray dried | 98.43 | 97.22 | na | 96.57 | 94.62 | 93.11 | 93.02 |
| 00197-60 | Budesonide, spray dried | 97.59 | 97.32 | na | ND | ND | 97.08 | 97.42 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

7. A method for treating a disease condition in a patient comprising the step of administering to the respiratory tract of the patient, an effective amount of the composition of claim 1.

8. The method of claim 1, wherein the dry powder composition is inhaled using a dry powder inhaler comprising a receptacle containing the composition.

9. The composition of claim 1, wherein the particles have a tap density of less than about 0.4 g/cm$^3$.

10. The composition of claim 1, wherein the particles have a fine particle fraction of at least 20% by weight.

11. The composition of claim 1, wherein the therapeutic-agent is budesonide.

12. The composition of claim 11, further comprising a buffering agent.

13. The composition of claim 12, wherein the buffering agent is a hydroxytricarboxylic acid or a salt thereof.

14. The composition of claim 13, wherein the buffering agent is sodium citrate.

15. The composition of claim 11, comprising budesonide in an amount from about 1% to about 10% by weight and polyalditol in an amount from about 65% to about 99% by weight of polyalditol and about 0% to about 25% by weight of sodium citrate.

16. A method of treating a patient suffering from an inflammatory disorder, comprising the step of administering by inhalation to the respiratory tract of the patient, an effective amount of the composition of claim 11.

17. The method of claim 16, wherein the inflammatory disorder is asthma, allergic rhinitis, infectious rhinitis, inflammatory bowel disease or nasal polypsis.

18. A kit for administration of a composition of claim 1, comprising at least one receptacle, wherein said receptacle comprises at least one unit dosage of the composition and wherein the receptacle is suitable for use with a dry powder inhaler.

19. A kit of claim 18, wherein the kit further comprises instructions for use.

\* \* \* \* \*

UNITED STATES PATENT AND TRADEMARK OFFICE
CERTIFICATE OF CORRECTION

| | | |
|---|---|---|
| PATENT NO. | : 8,614,255 B2 | Page 1 of 1 |
| APPLICATION NO. | : 12/195878 | |
| DATED | : December 24, 2013 | |
| INVENTOR(S) | : Charles D. Blizzard et al. | |

It is certified that error appears in the above-identified patent and that said Letters Patent is hereby corrected as shown below:

In the Claims

Column 22, Claim 2, line 13, please delete "polvalditol" and insert -- polyalditol --.

Signed and Sealed this
Twenty-ninth Day of April, 2014

Michelle K. Lee
*Deputy Director of the United States Patent and Trademark Office*